US00PP17774P3

(12) United States Plant Patent
Lowe

(10) Patent No.: US PP17,774 P3
(45) Date of Patent: May 29, 2007

(54) KIWI PLANT NAMED 'HORT51-1785'

(50) Latin Name: *Actinidia chinensis*
Varietal Denomination: Hort51-1785

(75) Inventor: Russell George Lowe, Te Puke (NZ)

(73) Assignee: The Horticulture and Food Research Institute of New Zealand Limited, Auckland (NZ)

( * ) Notice: Subject to any disclaimer, the term of this patent is extended or adjusted under 35 U.S.C. 154(b) by 15 days.

(21) Appl. No.: 11/122,613

(22) Filed: May 5, 2005

(65) Prior Publication Data

US 2006/0253946 P1 Nov. 9, 2006

(51) Int. Cl.
*A01H 5/00* (2006.01)

(52) U.S. Cl. ..... Plt./156

(58) Field of Classification Search ..... Plt./156
See application file for complete search history.

*Primary Examiner*—Anne Marie Grunberg
*Assistant Examiner*—S. B. McCormick-Ewoldt
(74) *Attorney, Agent, or Firm*—Greenlee Winner and Sullivan PC

(57) ABSTRACT

A new and distinct kiwi plant of the species *Actinidia chinensis* Planch. is described. The variety results from a controlled pollination using a female *A. chinensis* selection 'Jing Feng' (also known as 79-3, and by the accession code CK34_01) of unknown parentage, and a male *A. chinensis* selection CK40_02 of unknown parentage. Both parents ('Jing Feng' and CK40_02) are unpatented. The new variety is distinguished by its large globose-shaped fruit with a flat stylar end, golden coloured flesh and tangy sweet taste.

7 Drawing Sheets

Genus and species of plant claimed: *Actinidia chinensis*. Variety denomination: Hort51-1785.

BACKGROUND OF THE INVENTION

Kiwi plants in cultivation are mainly varieties of *A. deliciosa,* particularly 'Hayward' although some *A. chinensis* and *A. arguta* varieties are grown. *A. deliciosa* and *A. chinensis* are closely related and varieties of both types have large fruit (~100 g) with hair on the skin. The main varieties in New Zealand are 'Hayward' (*A. deliciosa*) and 'Hort16A' (*A. chinensis*). Fruit are usually cut and eaten with a spoon.

All *Actinidia* species are dioecious, so female varieties have to be interplanted with male pollinizers to ensure fruit production.

*A. chinensis* vines are deciduous and tend to grow vigorously in spring and summer when rapidly-growing shoots can intertwine and tangle if not managed. Vines do best in a mild warm-temperate climate without late spring or early autumn frosts. They produce consistently heavy crops when grown in well-drained fertile soils and given regular irrigation in dry spells.

*A. chinensis* flowers in spring (mid October–early December) in New Zealand. Harvest of *A. chinensis* fruit may occur between April and late-May in New Zealand depending on the selection and location of plantings.

SUMMARY OF THE INVENTION

The present invention is a new and distinctive kiwifruit variety having a generally globose shaped fruit with short, soft, silky hair and a golden yellow flesh when ripe. This new variety is designated 'Hort51-1785' and is derived from a controlled pollination using a female tetraploid *A. chinensis* selection 'Jing Feng' (also known as 79-3, and by the accession code CK34_01) of unknown parentage, and a male tetraploid *A. chinensis* selection CK40_02 of unknown parentage.

The female parent was introduced to New Zealand as vegetative plant material from Jiangxi, China. The male parent was selected in New Zealand from seedling plants raised from an introduction of seed from China in 1989. Both parents are unpatented.

This new variety was created during the course of a planned plant-breeding program, which was initiated during 1987 in Auckland, New Zealand. The cross was made on Nov. 24, 1994 in Te Puke, New Zealand. Seeds were sown in the winter of 1995 and 64 seedlings from this cross were planted out in the field at Te Puke in August 1996. The selection 'Hort51-1785' first flowered in November 1997 and fruit was first assessed in May 1998. Selection 'Hort51-1785' was grafted in 1998 onto four existing kiwifruit rootstocks in a clonal selection trial plot using graftwood from the original seedling plant.

The new variety can be asexually reproduced as cuttings or by grafting or budding on to seedling or cutting-grown rootstocks of *A. deliciosa* or *A. chinensis*. Trial plantings of grafted plants established at the Te Puke, Nelson and Kerikeri Research Centres in 1998 have shown that the unique combination of characters come true to form and are established and transmitted through succeeding asexual propagations.

'Hort51-1785' flowers at least two weeks later than Hort16A and requires specific tetraploid males to ensure adequate pollination.

Figure 1:
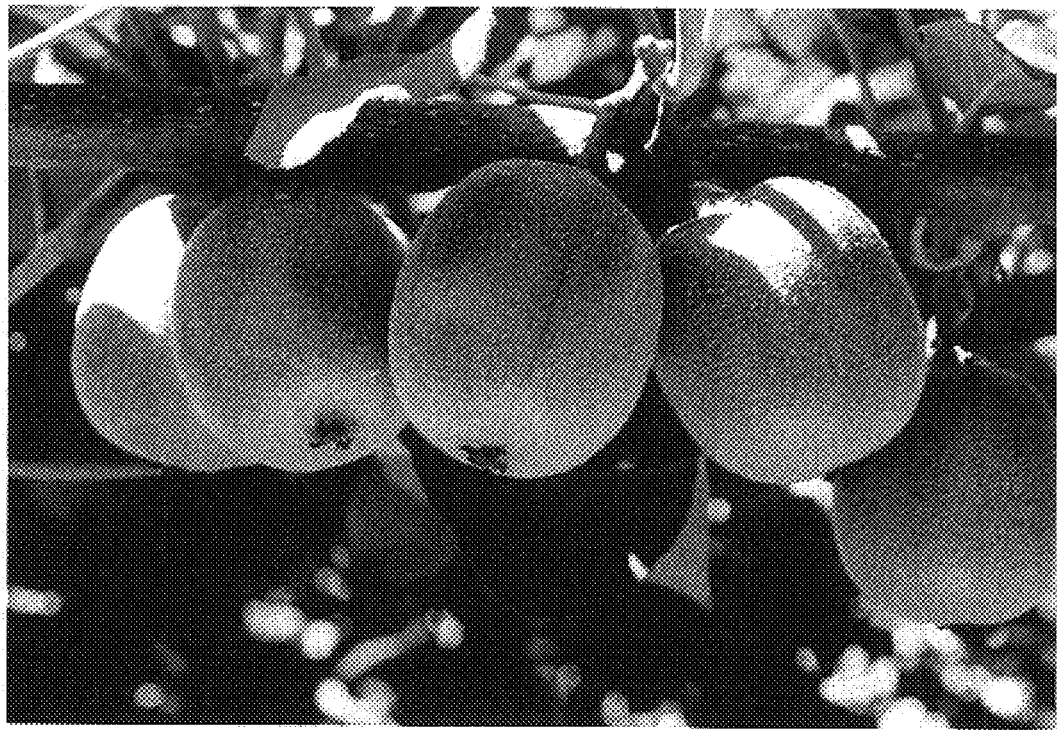
FIG. 1 shows typical fruit of 'Hort51-1785' on the vine.
Figure 2:
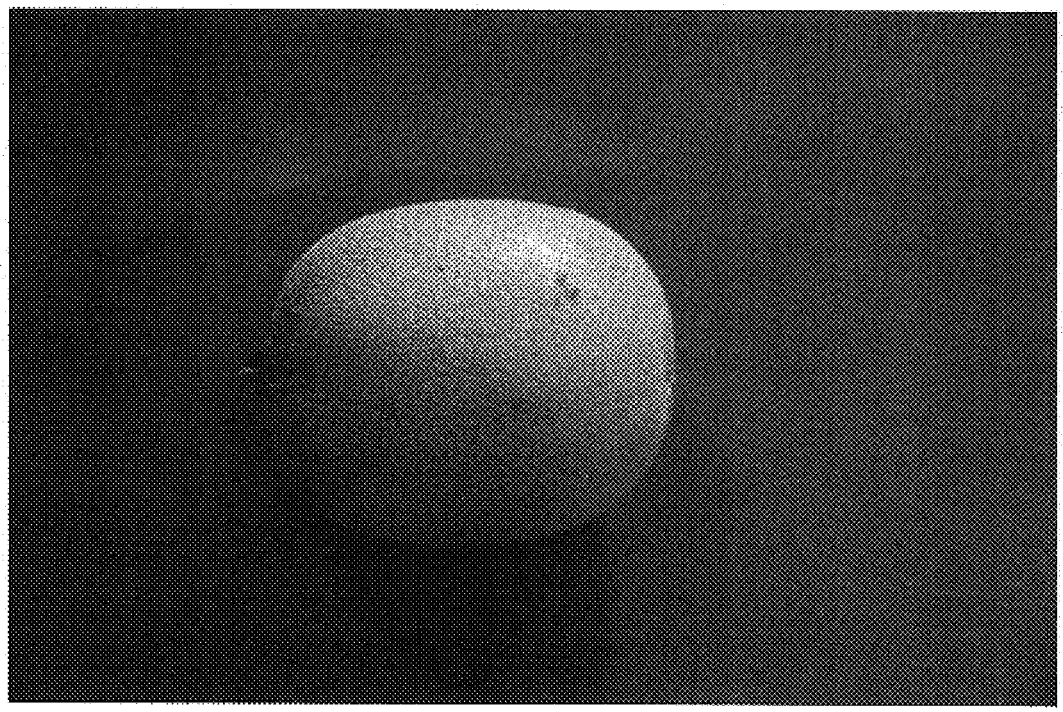
FIG. 2 shows typical fruit of 'Hort51-1785' in side profile.
Figure 3:
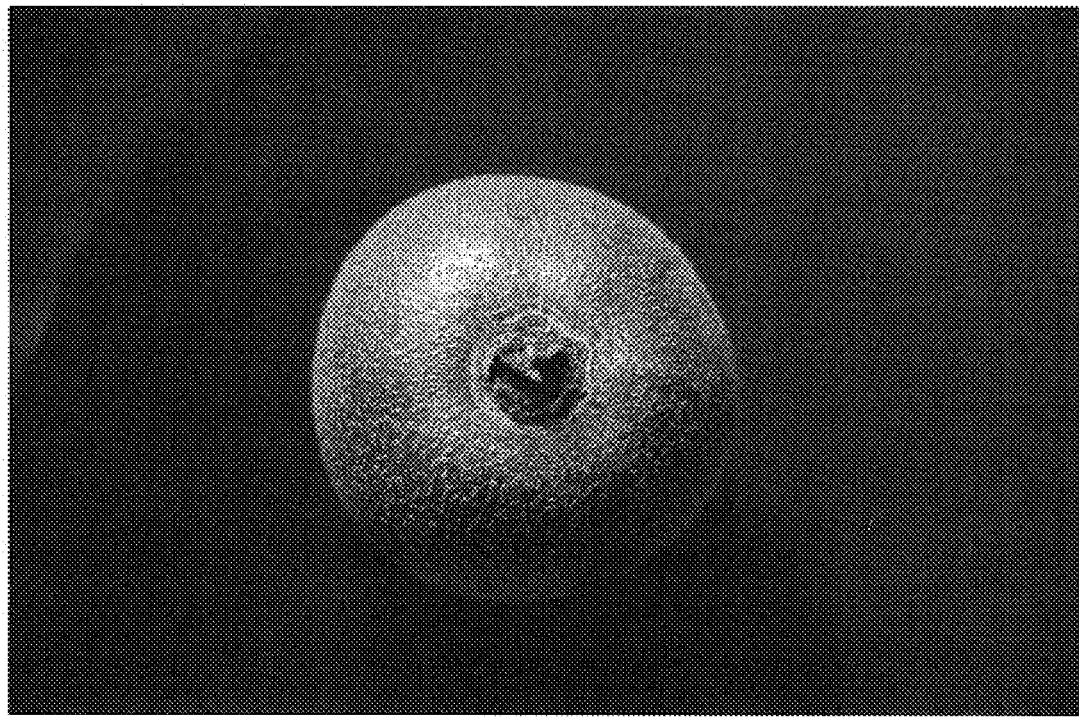
FIG. 3 shows a stem end view of fruit of 'Hort51-1785'.
Figure 4:
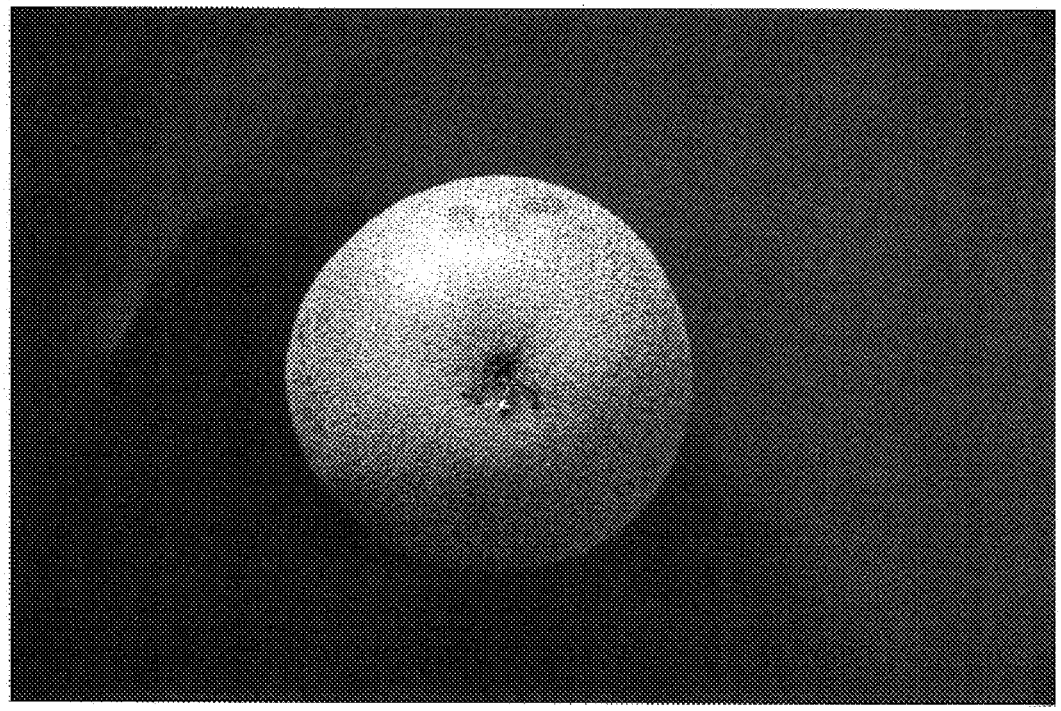
FIG. 4 shows a stylar end view of fruit of 'Hort51-1785'.
Figure 5:
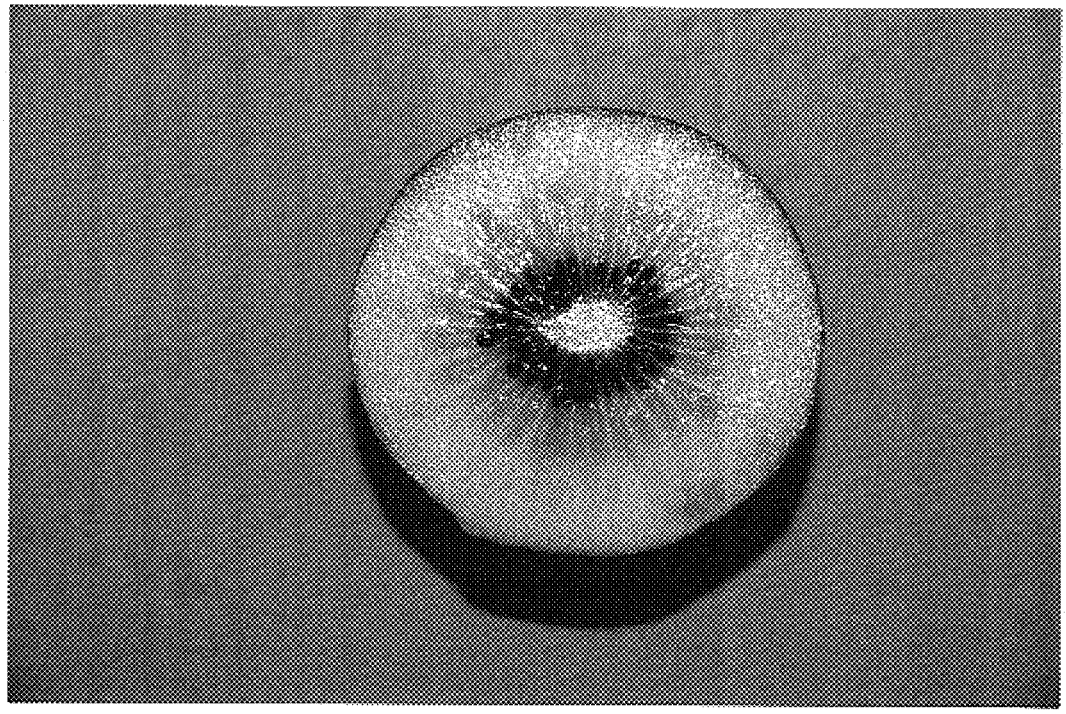
FIG. 5 shows fruit of 'Hort51-1785' in cross section.
Figure 6:
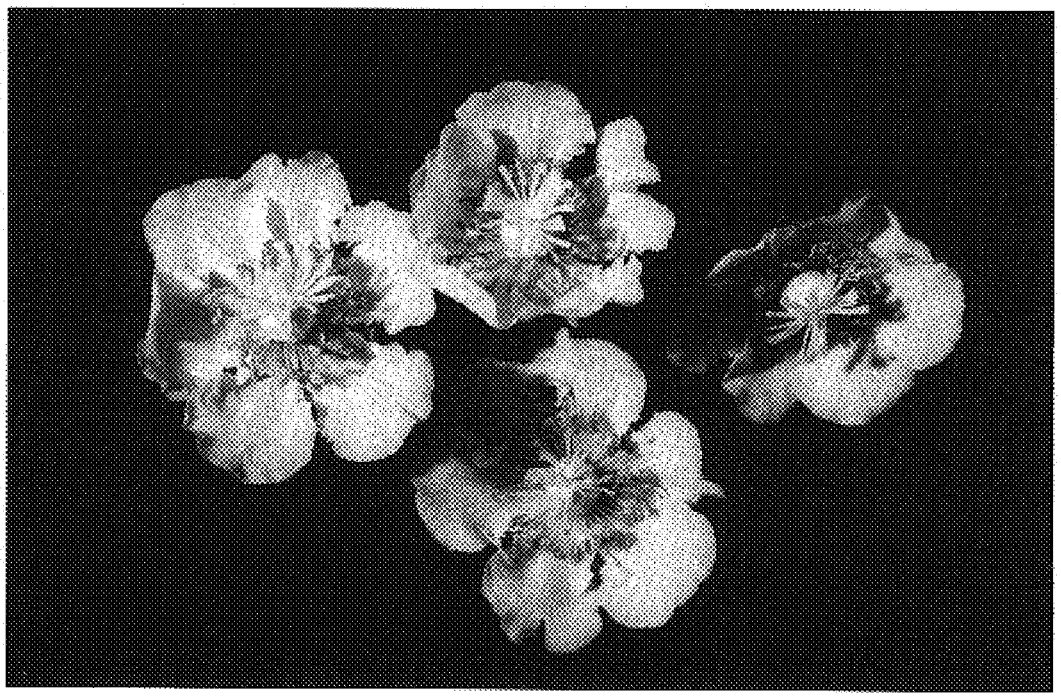
FIG. 6 shows flowers of 'Hort51-1785'.
Figure 7:
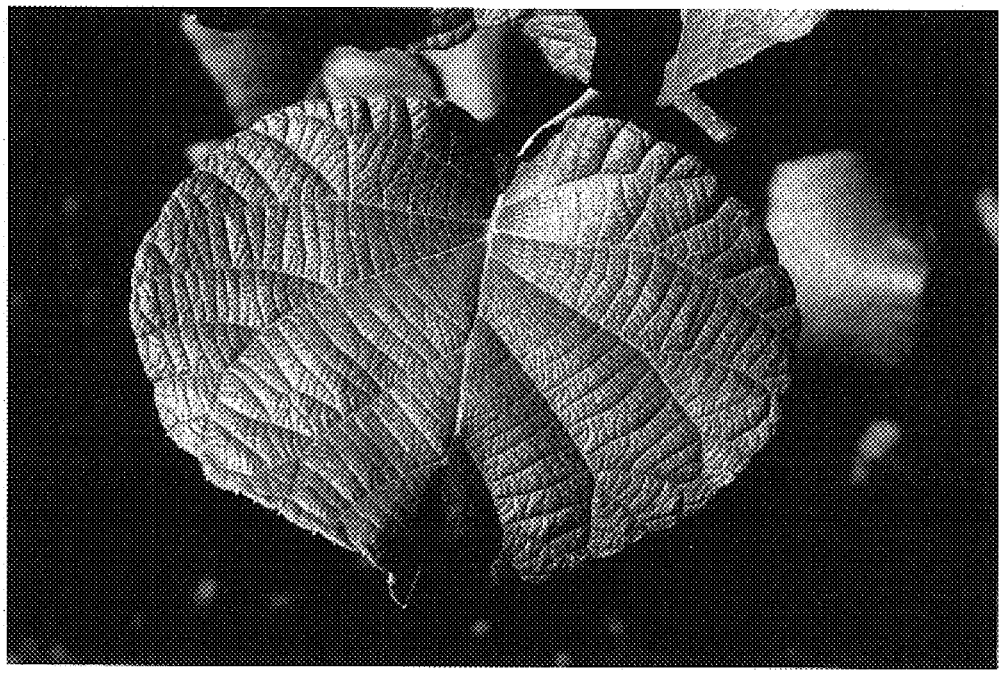
FIG. 7 shows the leaf of 'Hort51-1785'.

Photographs of fruit were taken at the normal harvest date. Fruit skin color may vary depending upon extent of exposure to direct sunlight.

DETAILED BOTANICAL DESCRIPTION

The new tetraploid kiwifruit variety 'Hort51-1785' is pistillate (female), and produces imperfect flowers, i.e. the flowers produce only sterile pollen and require a pollinizer to set fruit.

TABLE OF CHARACTERISTICS

Horticultural terminology is used in accordance with revised UPOV guidelines for kiwi. All dimensions are in millimeters, weights in grams (unless otherwise stated). Color references are in accord with the R.H.S. Colour Chart, the Royal Horticultural Society, London, 1966.

| | 'Hort51-1785' |
|---|---|
| PLANT | |
| (Measurements from samples of 10, unless stated) | |
| Plant: sex expression | female (flowers imperfect) |
| Plant: ploidy | tetraploid (2n = 2x = 116) |
| Plant: vigour | medium |
| Young shoot: hairs | present |
| Young shoot: density of hairs | medium |
| Young shoot: type of hairs | tomentose |
| Young shoot: anthocyanin coloration of growing tip | absent or very weak |
| Young shoot: anthocyanin coloration of leaf axil | absent or very weak |
| STEM | |
| Stem: coloration of leaf axil | absent or very weak |
| Stem: diameter | medium (mean 9.5 mm, range 7.6–10.5 mm at mid point[1]) |
| Stem: length | 1.2–1.8 m |
| Stem: dormant bud diameter | large (mean 6.3 mm, range 5.00–7.16 mm) |
| Stem: color on upper side of shoot | greyish-brown (near 177A to 199A) |
| Stem: character of bark | smooth |
| Stem: hairs | absent |
| Stem: conspicuousness of lenticels | conspicuous |
| Stem: number of lenticels/$cm^2$ bark area | mean 3.32/$cm^2$ (range 1.8–5.02/$cm^2$) |
| Stem: color of lenticels | brown, near 166C |
| Stem: size of lenticels - length | mean 3.27 mm, range 1.54–4.53 mm |
| Stem: size of lenticels - maximum width | mean 1.34 mm, range 0.82–2.03 mm |
| Stem: size of bud support | medium |
| Stem: visibility of bud (dormant canes) | visible |
| Stem: number of hairs visible on bud (dormant canes) | many |
| LEAF (Mature) | |
| Leaf: general shape of blade | very broadly ovate |
| Leaf: length | 124 mm |
| Leaf: width | 151 mm |
| Leaf: petiole length | 103 mm |
| Leaf: shape of tip of blade | acute |
| Leaf: shape of base of blade | cordate |
| Leaf: arrangement of leaf bases | overlapping |

-continued

| | 'Hort51-1785' |
|---|---|
| Leaf: puckering/blistering on upper side of blade | medium |
| Leaf: margin | ciliate |
| Leaf: green color of upper side of blade | medium green, near 147A |
| Leaf: glossiness of upper surface of blade | medium |
| Leaf: color of lower side of blade | light green, near 148B |
| Leaf: glaucosity (lower side of blade) | absent |
| Leaf: hairs on petiole | present |
| Leaf: density of hairs on petiole | medium |
| Leaf: anthocyanin coloration on upper side of petiole | medium |
| FLOWER | |
| Inflorescence: predominant number of flowers | three |
| Flower: pedicel hairs: | present |
| Flower: pedicel length of hairs | very short |
| Flower: pedicel length | mean 27.09 mm |
| Flower: number of sepals | six or seven |
| Flower: color of sepals | green, near 148D |
| Flower: length of sepals | mean 11.45 mm, range 8.86–12.37 mm |
| Flower: diameter of sepals | mean 9.09 mm, range 8.32–9.67 |
| Flower: diameter (terminal or king flower when fully open) | 51 mm (mean of 7 flowers) |
| Flower: mean number of petals per flower | 6 |
| Flower: length of petals | mean 28.77 mm, range 27.0–31.6 mm |
| Flower: width of petals | mean 23.89 mm, range 22.4–26.0 |
| Flower: ratio petal length/width | 1.21 |
| Flower: arrangement of petals | overlapping |
| Flower: petal shoulder | present |
| Flower: primary color of petals (when fully open) | white, near 155B |
| Flower: type of coloration of petals | bi-coloured, green at base |
| Flower: secondary color of base of petals | green, near 144D |
| Flower: filament color | white, near 157A |
| Flower: anther color | yellow, near 16C |
| Flower: attitude of styles | semi-erect |
| Flower: curvature of styles | absent |
| Flower: color of styles | white, near 155D |
| Flower: amount of hair on ovary | dense |
| Flower: colour of ovary | white near 157B |
| FRUIT | |
| Fruit: weight | mean 99 g |
| Fruit: length | 66 mm |
| Fruit: width (max) | 61 mm |
| Fruit: width (min) | 58 mm |
| Fruit: core diameter (max) | 12.4 mm |
| Fruit: core diameter (min) | 7.8 mm |
| Fruit: locule number | 30 |
| Fruit: peduncle length | 35 mm |
| Fruit: peduncle width | 3.9 mm |
| Fruit: general shape | globose |
| Fruit: cross section at median | circular |
| Fruit: general shape of stylar end | flat |
| Fruit: shape of shoulder on stalk end | squared |
| Fruit: presence of calyx ring | present |
| Fruit: expression of calyx ring | strongly expressed |
| Fruit: skin color at harvest (fruit still hard) | medium brown, near 199B |
| Fruit: skin colour change during ripening | absent |
| Fruit: skin color at maturity for consumption | medium brown, near 199B |
| Fruit: lenticel color at maturity | near 164C |
| Fruit: hairs | present |

-continued

| | 'Hort51-1785' |
|---|---|
| Fruit: density of hairs | sparse |
| Fruit: type of hairs | pubescent |
| Fruit: hair length | short |
| Fruit: concentration of hairs | uniform |
| Fruit: adherence of hairs to skin (when rubbed) | weak |
| Fruit: core diameter (at largest diameter) | small (approximately 12.4 mm) |
| Fruit: core shape (in cross section) | transverse elliptic |
| Fruit: core woody spike | weak |
| Fruit: prominence of core woody spike | small |
| Fruit: outer pericarp color at maturity for consumption | yellow, near 162D |
| Fruit: inner pericarp col. (locules) at mat. for consumption | yellow, near 162B |
| Fruit: core color at maturity | pale yellow, near 14D |
| Fruit: sweetness (Brix level) at maturity for consumption | 13.8% (range 11.4–16.2%) |
| Fruit: vitamin C content (45 fruit sample) | 133 mg/100 g fresh weight (range 123–140 mg/100 g fresh weight) mean of 5 plants, 3 values, per plant. |
| Fruit: seed colour at maturity (in flesh) | blackish-brown, near 200A |
| Fruit: seed colour when dry | dark brown, near 200C |
| Fruit: average seed number per fruit | mean 514, range 465–596 |
| Fruit: seed length | mean 2.45 mm |
| Fruit: seed maximum diameter | mean 1.71 mm |
| EVENTS | |
| Time of vegetative budbreak | medium (mid September) |
| Time of beginning of flowering | 8 Nov. (2004) |
| Time of maturity for harvest (at nominated Brix level) | last week of May (Brix 10%) under New Zealand growing conditions |

[1]Measured in the middle of the cane i.e. halfway down the full length and midway between two buds.

Observations were made on plants growing at Te Puke, New Zealand. These plants had been grafted on to seedling kiwifruit rootstocks.

Rootstocks: 'Hort51-1785' vines can be grown on the same rootstocks as 'Hort16A'. Rootstocks currently being used in New Zealand include *A. deliciosa* and *A. chinensis* seedlings, 'Hayward' (not patented) and 'Kaimai' (not patented) rooted cuttings.

Cropping: Young vines of 'Hort51-1785' crop heavily when young, and must be thinned directly after fruit set to reduce crop loads and to ensure fruit size is not compromised by over cropping. Vines of 'Hort51-1785' begin to bear fruit in their second year from graft and can be expected to reach full capacity at about 5 years.

Storage life: The storage life of 'Hort51-1785' fruit is 20 weeks at 0° C., if stored in unventilated containers.

Pest and disease resistance/susceptibility: Unsprayed fruit of 'Hort51-1785' is slightly more susceptible to Greedy Scale infestation, but less damaged by Leaf Roller caterpillar compared to 'Hayward'. Flowers of 'Hort51-1785' are more susceptible to fungal *Sclerotinia* infection during wet weather, possibly due to the higher flower density (three flowers per inflorescence) compared to 'Hayward' (single flowers).

OTHER DATA

Fruit size: Date gathered from harvesting all fruit, from 6 vines, in May 2004.

| | | | | | |
|---|---|---|---|---|---|
| Mean fruit weight: | 99.2 g | maximum: | 138 g | minimum: | 73 g |
| Mean fruit number: | 332 | maximum: | 1084 | minimum: | 102 |
| Mean yield: | 38.8 kg | maximum: | 14.1 kg | minimum: | 81.4 kg |

FRUIT FLESH AND SKIN COLOR MEASUREMENT

Color chart: R.H.S. Colour Chart, The Royal Horticultural Society, London, 1966.

| | |
|---|---|
| Fruit: core color at harvest | 150C to 150D |
| Fruit: seed color (in flesh) | 200A |
| Fruit: seed colour (dry seed) | 200C |
| Fruit: skin color at maturity | 199B |
| Leaf: color of upper side (in mature leaf after petal fall) | 147A |
| Leaf: color of lower side (in mature leaf after petal fall) | 148B |
| Plant stem: color on exposed side | 177A to 199A |

COMPARISON TO CLOSEST CULTIVAR

The distinctive characteristics of this new kiwifruit variety, described in detail below, were observed in 2005 at Te Puke, New Zealand. The age of the plants was 6 years from grafting onto seedling rootstocks.

Comparison with similar varieties 'Hort16A' (U.S. Plant Pat. No. 11,066) and 'KI 89' (U.S. Plant Pat. No. 8,497) shows that 'Hort51-1785' may be distinguished as follows in Table 1.

TABLE 1

Comparison with similar varieties
Color references are in accord with the RHS Colour Chart, the Royal Horticultural Society, London, 1966. Observations made under New Zealand growing conditions.

| Characteristic | 'Hort51-1785' | 'Hort16A' | 'KI 89' |
|---|---|---|---|
| Time of full bloom | late November | mid October | early November |
| Fruit: Color of skin | mid-brown, near 199B | yellow-brown, near 199A/161A | reddish-brown, near 164B/164C |
| Fruit: mean weight | 99 g | 91 g | 103.4 |
| Fruit: Core diameter (maximum) | very small (approximately 12.4 mm) | small (approximately 13.08 mm) | medium (approximately 15.3 mm) |
| Fruit: General shape | globose | ovoid | cylindrical |
| Fruit: shape at stylar end | rounded | protruding | slightly depressed |
| Fruit: presence of internal stylar cavity | present | not present | not present |

TABLE 1-continued

Comparison with similar varieties
Color references are in accord with the RHS Colour Chart, the Royal Horticultural Society, London, 1966. Observations made under New Zealand growing conditions.

| Characteristic | 'Hort51-1785' | 'Hort16A' | 'KI 89' |
|---|---|---|---|
| Fruit: Flesh color (ripe) | golden yellow, near 162D | yellow, near 12C/12B | yellow-green, near 145C/154D |
| Fruit: Presence of lenticels on skin | present | not present | not present |
| Fruit: Visibility of lenticels on skin | conspicuous | not obvious | not obvious |
| Fruit: Mean soluble solids content when ripe | 12.5–14% | 14–19% | 10.8–12.4% |
| Mean dry matter at harvest | 17.8% | 18.3% | 15.5–17.2% |
| Mean flesh firmness at harvest | 6.8 Kgf | 4.6 Kgf | 3.7 Kgf |

Fruit of 'Hort51-1785' is globose in shape with a rounded stylar end compared with the ovoid shape and protruding stylar beak of 'Hort16A'. The flesh of 'Hort51-1785' is golden yellow when ripe compared to the lighter yellow flesh of 'Hort16A' and the yellow-green flesh of 'KI 89'. The skin of 'Hort51-1785' is a pale mid-brown color, whereas the skin of 'Hort16A' is yellow-brown and that of 'KI 89' is reddish-brown. The fruit of 'Hort51-1785' has conspicuous, raised lenticels on the skin, 'Hort16A' and 'KI 89' do not have raised lenticels.

The fruit of 'Hort51-1785' is generally larger sized, has lower brix, lower dry matter content, and higher flesh firmness at harvest than 'Hort16A'. The fruit of 'Hort51-1785' is generally shorter but of greater diameter than fruit of either 'Hort16A' or 'KI 89'.

TABLE 2

Comparison with female parent, 'Jing Feng'
Colour references are in accord with the RHS Colour Chart, the Royal Horticultural Society, London, 1966. Observations made under New Zealand growing conditions.

| Characteristic | 'Hort51-1785' | 'Jing Feng' |
|---|---|---|
| Time of full bloom | late November | late November |
| Fruit: color of skin | mid-brown, near 199B | light brown, near 165B |
| Fruit: core diameter | 12.4 mm | 14.1 mm |
| Fruit: general shape | globose | ellipsoidal |
| Fruit: ratio of fruit maximum width/fruit length | 0.92 | 0.78 |
| Fruit: mean weight | 99 g | 103 g |
| Fruit: shape at stylar end | rounded | flat |
| Fruit: presence of stylar cavity | present | not present |
| Fruit: flesh color | golden yellow near 162D | golden yellow, near 163D |
| Fruit: locule color | near 162B | near 164B |
| Presence of lenticels on fruit skin | present | not present |
| Visibility of lenticels on fruit skin | conspicuous | not obvious |
| Mean soluble solids content of ripe fruit | 12.5–14% | 11.6–14.6% |
| Mean dry matter at harvest | 17.8% | 16.6% |
| Mean firmness at harvest | 6.8 Kgf | 5.5 Kgf |

The most striking difference between 'Hort51-1785' and the female parent 'Jing Feng' is that of fruit shape. 'Hort51-1785' has globose-shaped fruit with a ratio of maximum width/fruit length of 0.92 whereas 'Jing Feng' fruit is ellipsoidal in shape with a ratio of maximum width/fruit length of 0.78. 'Hort51-1785' fruit have a small internal cavity, average length 10.2 mm, at the stylar end, whereas 'Jing Feng' fruit has no cavity.

I claim:

1. A new and distinct kiwi plant of the species *A. chinensis* substantially as herein illustrated and described.

* * * * *